United States Patent
Jenkner et al.

(10) Patent No.: US 8,787,559 B2
(45) Date of Patent: Jul. 22, 2014

(54) CODEC CIRCUIT FOR POTS SYSTEM

(75) Inventors: Christian Jenkner, Velden (AT);
Gerhard Noessing, Villach (AT);
Richard Gaggl, Poertschach (AT);
Joachim Pichler, Landskron (AT)

(73) Assignee: Lantiq Deutschland GmbH, Neubiberg (DE)

( * ) Notice: Subject to any disclaimer, the term of this patent is extended or adjusted under 35 U.S.C. 154(b) by 357 days.

(21) Appl. No.: 13/406,567

(22) Filed: Feb. 28, 2012

(65) Prior Publication Data

US 2012/0155632 A1 Jun. 21, 2012

Related U.S. Application Data

(63) Continuation of application No. 11/623,283, filed on Jan. 15, 2007, now Pat. No. 8,243,916.

(51) Int. Cl.
*H04M 3/00* (2006.01)
*H03M 3/00* (2006.01)

(52) U.S. Cl.
USPC .......................... 379/399.02; 341/143

(58) Field of Classification Search
None
See application file for complete search history.

(56) References Cited

U.S. PATENT DOCUMENTS

2002/0118818 A1* 8/2002 Miller et al. ............. 379/387.02
2004/0202310 A1* 10/2004 Li ................................ 379/377

* cited by examiner

*Primary Examiner* — Fan Tsang
*Assistant Examiner* — Jeffrey Lytle

(57) ABSTRACT

A CODEC circuit for POTS system comprises a digital circuit for outputting a digital control signal having a first bit width, the digital control signal being indicative of a voltage to be applied to a POTS subscriber line pair. Further, the CODEC comprises a noise shaper coupled to an output of the digital circuit for generating a noise-shaped control signal and a digital-to-analog converter coupled to an output of the noise shaper, the input of the digital-to-analog converter having a second bit width being larger than 1 and smaller than the first bit width.

39 Claims, 4 Drawing Sheets

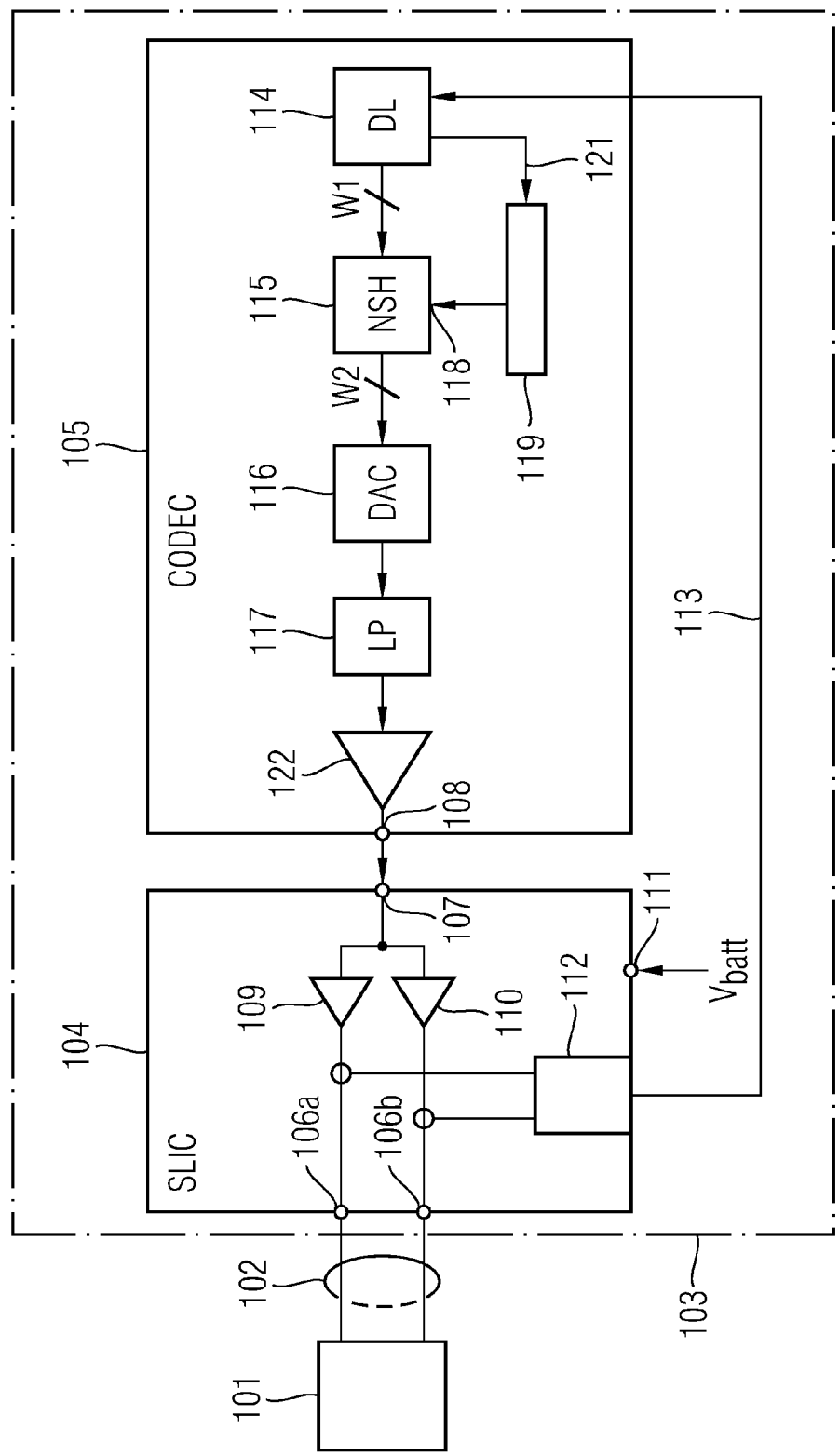

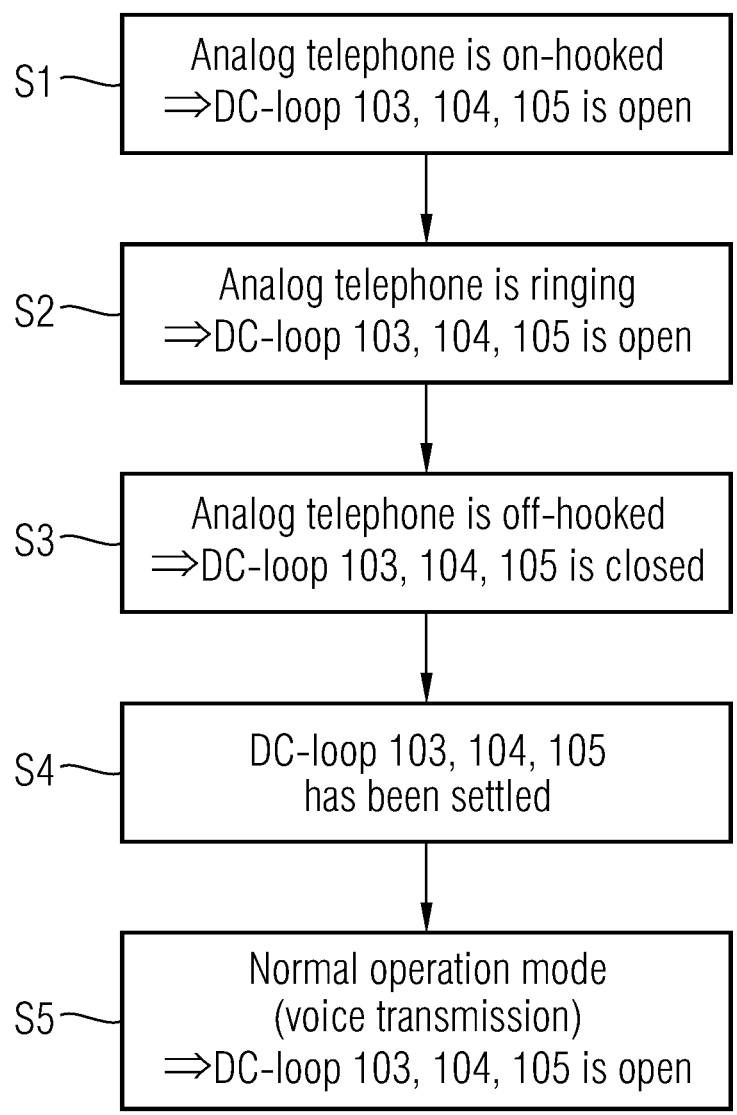

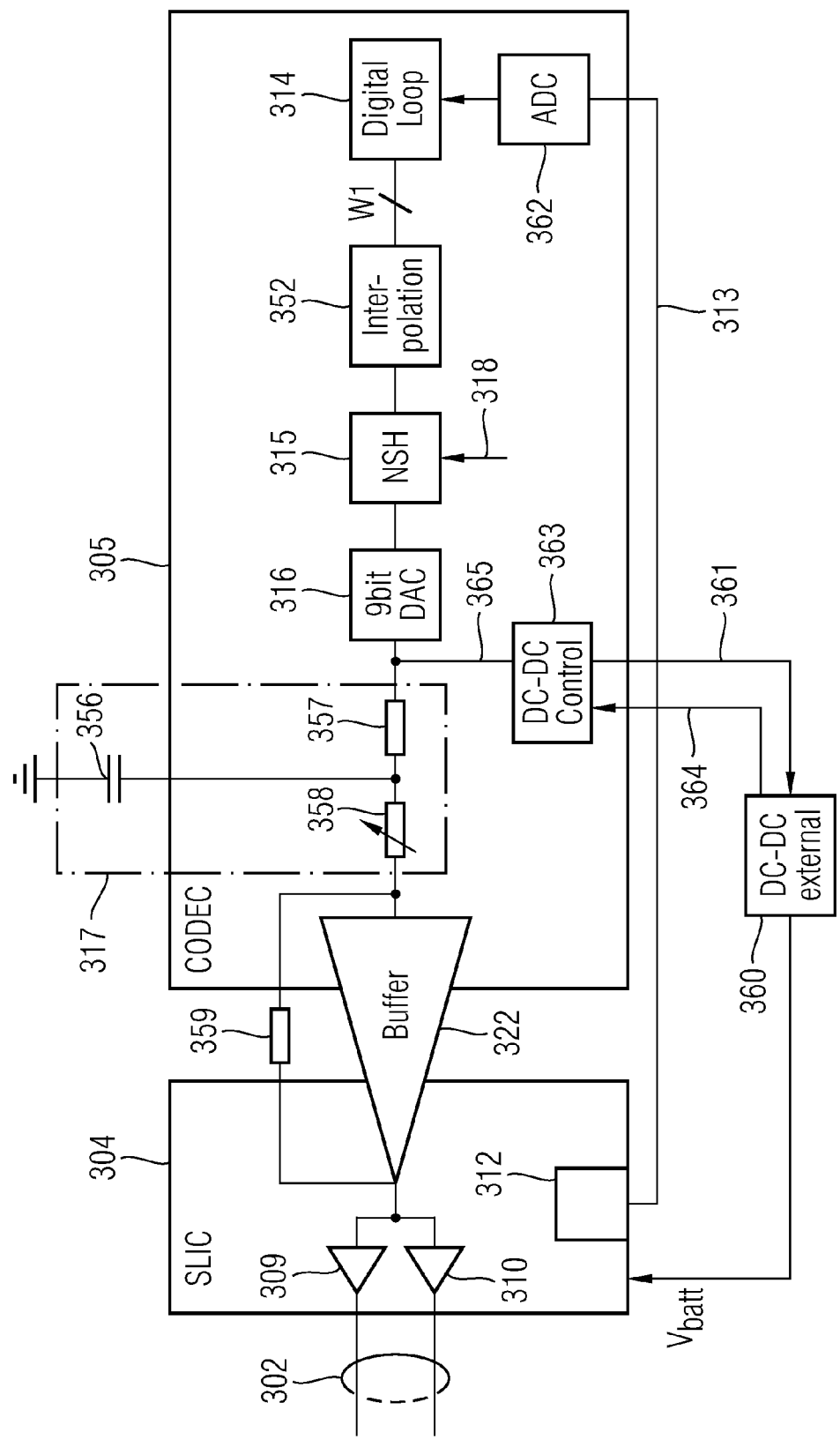

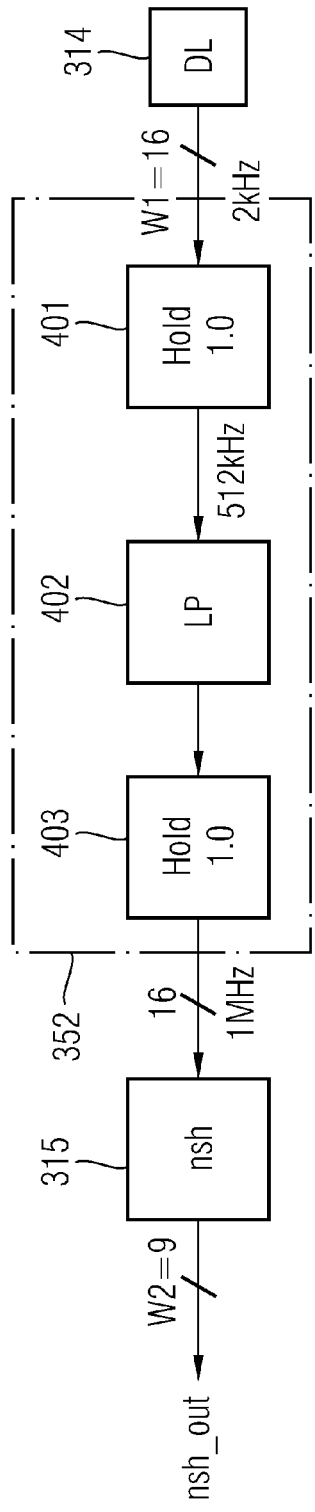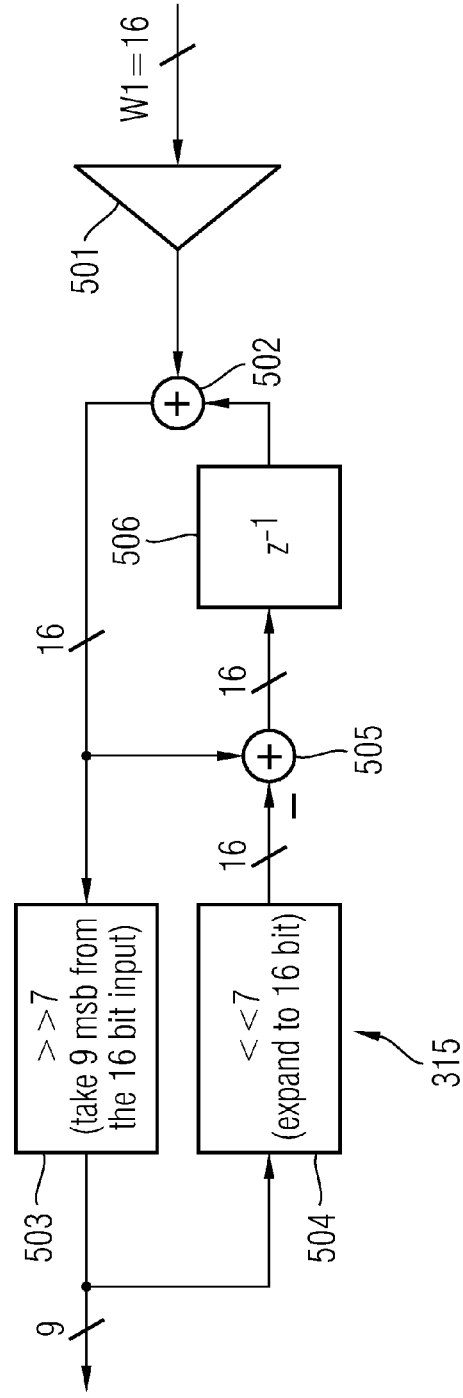

CODEC CIRCUIT FOR POTS SYSTEM

This application is a Continuation Application of U.S. patent application Ser. No. 11/623,283 entitled "Codec Circuit for POTS System", filed on Jan. 15, 2007, now U.S. Pat. No. 8,243,916 B2.

BACKGROUND OF THE INVENTION

The invention relates in general to telecommunication systems and circuits therefore and more particularly to a supply voltage feeding circuit that is configured to provide a supply voltage for a POTS (Plain Old Telephone Service) subscriber line pair.

In POTS systems, an analog telephone is coupled via a subscriber line pair to a telephone exchange. As the analog telephone does not have its own voltage supply, it is operated by a direct current received from the telephone exchange via the subscriber line pair. To this end, the telephone exchange comprises a supply voltage feeding circuit for generating a direct voltage and applying it to the subscriber line pair. By off-hooking the analog telephone, a contact closes and the supply voltage causes the supply current to flow through the subscriber line pair and to power the analog telephone.

At the telephone exchange, the supply of DC voltage on the subscriber line pair has to be regulated in order to maintain a certain current to feed or bias the analog telephone. Therefore, the DC current on the subscriber line pair is detected and the supply voltage feeding circuit for controlling the DC voltage applied to the subscriber line pair comprises a feedback loop which regulates the DC voltage in response to the detected current flowing through the subscriber line pair. In other implementations, this feedback loop may be formed for detecting the line voltage and feeding a line current. Voltage regulation is known as "battery feeding" and is performed continuously during the whole period of the call. Therefore, line feeding noise generated by the supply voltage feeding circuit has to be minimized. Typically, this is done by a low pass filter blocking AC signal contributions from entering the subscriber line pair.

Besides battery feeding, the supply voltage feeding circuit in the telephone exchange has to provide the ring functionality. During ringing, a low frequent AC voltage in the range of 15 Hz to 60 Hz is fed to the subscriber line pair. However, the low pass filter used for filtering off the line feeding noise may undesirably impair or even block the AC ring signal. As a result, it may be necessary to use a low pass filter with variable cut-off frequency or otherwise to increase the complexity of the circuit in order to guarantee for low noise battery feeding as well as effective ringing.

BRIEF DESCRIPTION OF THE SEVERAL VIEWS OF THE DRAWINGS

Aspects of the invention are made more evident in the following detailed description of some embodiments when read in conjunction with the attached drawing figures, wherein:

FIG. 1 is a generic block diagram of a DC battery feeding circuit used in a POTS telephone exchange;

FIG. 2 is a flow diagram illustrating a battery feeding DC voltage generation process;

FIG. 3 is a block diagram of a battery supply voltage feeding circuit according to an embodiment of the invention;

FIG. 4 is a block diagram of an interpolator and noise shaper; and

FIG. 5 is a schematic diagram of a noise shaper.

DETAILED DESCRIPTION OF THE INVENTION

FIG. 1 shows a circuitry of a POTS system comprising a POTS analog terminal device 101, e.g. an analog telephone, which is connected via a two-wire twisted line 102 to a telephone exchange 103, e.g. a local exchange or a branch exchange. The telephone exchange 103 comprises, inter alia, a SLIC (Subscriber Line Interface Circuit) 104 and a CODEC (COder/DECoder) circuit 105.

The SLIC 104 has two output terminals (often termed "tip" and "ring") 106a, 106b which are connected to the two wires 102 of the subscriber line pair. At these two terminals 106a, 106b the SLIC 104 provides for the DC feeding voltage for powering the terminal device 101. Without loss of generality, in the following, the terminal device 101 is assumed to be an analog telephone. When the telephone 101 is not in use, the receiver is hung on a spring-loaded hook causing an electrical contact disconnecting the telephone 101 from the lines 102. The telephone 101 is said to be "on hook". When the receiver is taken from the hook, the telephone is said to be "off hook", the electrical contact is closed and the telephone 101 is powered by a DC line current flowing through the lines 102. Typically, a DC line current of about maximum 20 mA is needed. The SLIC 104 and CODEC circuit 105 arrangement is used to provide for an appropriate DC voltage at the terminals 106a, 106b necessary for driving the telephone 101 with this certain target current. Customarily, the SLIC 104 may generate a maximum DC voltage of 48 V during operation. However, especially in the case when the distance between the telephone exchange 103 and the analog telephone 101 is not too far, a DC voltage of about 25 V may be sufficient to maintain the required DC target current.

The SLIC 104 comprises an input 107 which is connected to an output 108 of the CODEC circuit 105. The CODEC circuit 105, which is explained later in more detail, may be implemented in CMOS technology and thus provides for an output signal of approximately maximum 3.3 V. The SLIC 104 has to amplify this output signal from the CODEC circuit 105 to the comparatively high DC output voltage needed at output terminals 106a, 106b of the SLIC 104. To this end, the SLIC 104 comprises two line drivers (amplifiers) 109, 110 for driving the subscriber lines 102. These line drivers 109, 110 are powered by a supply voltage $V_{batt}$ which is externally generated and fed into the SLIC 104 at a battery voltage input 111. $V_{batt}$ has to be greater than the DC output voltage between terminals 106a, 106b. Typically, SLIC 104 is implemented as an integrated circuit designed in a technology which is suitable for high voltage transistor switching applications.

During normal mode operation (i.e. transmission of a voice signal), an AC signal contribution representing voice is superimposed or modulated onto the DC supply voltage signal of usually maximum 48 V. During ringing, the ring signal is also supplied over the subscriber line pair 102 to the analog telephone 101. In case of ringing, the SLIC 104 should be capable of generating a periodic, e.g. sinusoidal or trapezoidal signal of a peak voltage of up to 150 V.

The SLIC 104 comprises a current detector 112 for detecting the DC current flowing through the subscriber line pair 102. The current detector 112 outputs a quantity which is representative of this current. This quantity is fed back over feedback line 113 to a digital loop (DL) circuit 114 being part of the CODEC circuit 105. Further, the CODEC circuit 105 may comprise a noise shaper (NSH) 115, a digital-to-analog converter (DAC) 116, a low pass (LP) filter 117 and a DC buffer 122 arranged in the aforementioned order in the signal path of the CODEC circuit 105.

The digital loop circuit 114 may be a micro-controller programmed to compare the quantity representative of a DC line current with a target line current and outputting a control variable which depends on the deviation between the compared quantities. As it is known in feedback control theory, the control variable should be calculated such that the actual DC line current is adjusted to be equal to the target DC line current. The digital control variable is indicative of a DC line voltage needed to properly adjust the DC line current.

The control variable output by the digital loop circuit 114 is represented by a digital signal having a first bit width w1. This digital signal is input to the noise shaper 115. The noise shaper 115 reduces the bit width w1 of the input signal to a bit width w2<w1 at an output of the noise shaper 115. Concurrently, the noise shaper 115 minimizes a quantization error. As known in the art, noise shaping is accomplished by putting the quantization error in an internal feedback loop. In this feedback loop, the quantization error is filtered resulting in that noise in the output signal is shifted to higher frequencies.

The DAC 116 having an input bit width of w2 is coupled to the output of the noise shaper 115. The DAC 116 converts the output of the noise shaper 115 into an analog output signal.

The analog output signal of the DAC 116 is filtered by the low pass filter 117 and passed via DC buffer 122 to the output 106 of the CODEC circuit 105.

The noise shaper 115 allows to use a DAC 116 with a moderate or low input bit width (for example w2=9 bit) in combination with a low pass filter 117 which has a cut-off frequency of several hundreds Hz, for instance 1 KHz. This considerably reduces the circuit complexity and the costs of the CODEC circuit 105.

Basically, referring to conventional CODEC circuits, in which no noise shaper is provided, a DAC with a low resolution of e.g. 9 bit would require to be followed by a low pass filter with a cut-off frequency of about 20 Hz in order to effectively attenuate the high quantization noise caused by the DAC. This, on the other hand, would block any ring signal having a frequency of about 15 Hz to 60 Hz. Therefore, CODEC circuits with low resolution DACs need to implement a switchable low pass filter which is switched during the ring mode to a higher cut-off frequency. Alternatively, still in the conventional art without noise shaper, a DAC with high resolution (e.g. w2=16) could be used. In this case, the low pass filter could have a higher cut-off frequency because quantization noise is reduced by the enhanced resolution of the DAC. However, a high resolution DAC is expensive because of the large die area needed. Therefore, by shifting the quantization noise to higher frequencies, the combination of the noise shaper 115 and the low resolution DAC 116 provides for reduced quantization noise in the low frequency range of interest, thus allowing to relax the cut-off frequency of the low pass filter 117 up to some hundred Hz. Thus, it is not necessary to switch the low pass filter 117 during the ring mode to a higher cut-off frequency.

In the ring mode an sinusoidal ring signal may be added to the digital signal at the input of the DAC 116 or at another node in the signal path of the CODEC circuit 105. In normal operation mode (i.e. during voice transmission), a voice signal is modulated as an AC contribution to the control signal for DC voltage supply in the signal path upstream of the SLIC 104. For instance, this may be accomplished by a separate DAC (not shown) and by superimposing the analog output signal of the CODEC circuit 105 with the analog AC voice output signal of the separate DAC.

The noise shaper 115 may be enabled/disabled at input 118 by a control signal which is generated in an on/off circuit 119. The on/off circuit 119 detects whether or not the DC loop represented by CODEC circuit 105, SLIC 104 and feedback line 103 is settled. If the DC loop 103, 104, 105 is settled, the on/off circuit 119 switches the noise shaper 115 off, whereby the final digital output word at the output of the noise shaper 115 (or the final digital input word at the input of the DAC 116) is frozen. In this condition, the DC loop 103, 104, 105 is open and the DAC 116 operates on a fixed input digital word. As a result, any DAC switching noise (i.e. quantization noise) is inhibited and only the static DAC noise is sent via SLIC 104 to the subscriber lines 102.

One possibility of monitoring the DC loop 103, 104, 105 in view of its transient response (settlement condition) is to detect, for instance, if the remaining error in the DC loop 103, 104, 105 is below a certain tolerable value. If the remaining error is low enough, the on/off circuit 119 may switch off the noise shaper 115. Monitoring of the remaining error is done in the digital loop circuit 114. Further, for again enabling the noise shaper 115, the on/off circuit 119 may receive a command signal from the digital loop circuit 114 via line 121. It is to be noted that a variety of other possibilities for monitoring the transient response of DC loop 103, 104, 105 is possible and readily available for a person skilled in the art.

FIG. 2 illustrates in an exemplary manner a method for signal processing according to an embodiment. In a first step S1, the analog telephone is on-hooked. In this situation, the DC loop 103, 104, 105 is open.

During the ring operation (step S2) the DC loop 103, 104, 105 is open. During ringing, the CODEC circuit 105 outputs a periodic (e.g. sinusoidal) control signal of a few volt which is amplified in SLIC 104 up to, for instance, 150 V.

When the analog telephone 101 is hooked off, step S3, the DC operating current starts to flow through the subscriber lines 102. The current flow is regulated by closed DC loop 103, 104, 105 to a desired target current value.

When the DC loop 103, 104, 105 has been settled (step S4), the DC loop 103, 104, 105 may be opened again (step S5). To this end, during normal operation mode (i.e. voice transmission), the noise shaper 115 may be disabled (however, still outputting the frozen final digital word for further processing in the DAC 116). Disabling the noise shaper 115 is beneficial in view of noise reduction and low power consumption.

FIG. 3 illustrates an embodiment of a SLIC/CODEC arrangement according to the principles outlined above in conjunction with FIGS. 1 and 2. Thus, the above description may be analogously applied to the embodiment presented in FIG. 3 and vice versa.

SLIC 304 contains line drivers 309 and 310 corresponding to line drivers 109, 110 of FIG. 1. A current detector 312 corresponding to current detector 112 (FIG. 1) detects the line current and sends a scaled image of the line current to the CODEC circuit 305 via feedback line 313. There, the current information is converted to a voltage (not shown), and an analog-to-digital converter (ADC) 362 is provided for converting this voltage to a digital signal processed by the digital loop circuit 314.

The digital loop circuit 314 corresponds to digital loop circuit 114. It may have an output sampling rate of 2 kHz and a bit width of w1=16. The output of the digital loop circuit 314 is connected to an oversampling unit 352, which is illustrated in more detail in FIG. 4. The oversampling unit 352 uses a first interpolator 401 for enhancing the sampling rate up to 512 kHz. Interpolation may be done by a first order hold operation.

The interpolated signal is fed into a low pass (LP) filter 402. The low pass filter 402 may be a third order wave digital filter. Wave digital filters are easy to implement and provide a high quality factor even at lower orders. Basically, any low pass filter type may be used. The low pass filter 402 is effective for mirror frequency suppression.

The filtered signal is input to a second interpolator 403. The second interpolator 403 interpolates the filtered signal to a sampling frequency of 1 MHz. Again, a first order hold interpolation operation may be used.

An input of a noise shaper 315 corresponding to the noise shaper 115 shown in FIG. 1 is coupled to the output of the oversampling unit 352. The noise shaper 315 reduces the bit width e.g. from w1=16 to w2=9. With this arrangement, the switching noise of a low resolution (e.g. 9 bit) DAC 316 coupled to the output of the noise shaper 315 and corresponding to the DAC 116 in FIG. 1 can be significantly reduced.

The DAC 316 may be implemented as a binary weighted DAC, for instance as a R-2R ladder DAC, which is a binary weighted DAC that uses a repeating cascaded structure of resistor values R and 2R. The output bit width of the DAC 316 may be chosen as a compromise between resolution and implementation effort. The resolution should only be high enough to provide for sufficient static adjustability of the output voltage produced by the SLIC 304. For example, a 9 bit DAC meets this requirement. However, a 9 bit DAC has still a considerable quantization error great enough that during normal operation mode, the toggling of the LSB at the output of the DAC may possibly be heard by a user using the analog telephone 101. If the noise shaper 315 is designed to have the capability of being switched off at input 318 by a control signal which may be generated as described in conjunction with FIG. 1, the toggling of the LSB is inhibited. Thus, the possibility of switching on/off the noise shaper 315 during normal operation mode not only reduces the current consumption but moreover saves costs which otherwise would possibly be needed for implementing a higher resolution DAC which is able to guarantee a "silent" regulation performance.

Capacitor 356 and resistor 357 and 358 establish a low pass filter 317 corresponding to low pass filter 117 in FIG. 1. The low pass filter 317 has a cut-off frequency of e.g. 1 kHz. Lower values of e.g. 100 Hz or 500 Hz or higher values may also be possible. Capacitor 356 is typically external to the CODEC chip because otherwise, it would consume too much silicon area. It may have for instance a capacity of about 68 nF.

An adjustable resistor 358 is coupled to the output of the low pass filter 317. The adjustable resistor 358 is used for adjusting the gain of the CODEC circuit 305. The gain of the CODEC circuit 305 may be different for the ring mode and the normal operation mode. Also the cut-off frequency of the low pass filter 317 is changed by the value change of resistor 358, but this will not have a negative effect on the ring signal, since the ring signal is in any case within the pass-band of the low pass filter 317.

A shared buffer 322 is connected between the output of the adjustable resistor 358 and the input of the line drivers 309, 310. The shared buffer 322 is depicted in FIG. 3 in a somewhat symbolic manner bridging the CODEC integrated circuit and the SLIC integrated circuit. Technically, this means that an input stage of the shared buffer 322 is located in the CODEC integrated circuit (and thus is implemented in cost effective CMOS technology) whereas a high voltage output stage of the shared buffer 322 is implemented in the SLIC integrated circuit. The output of the shared buffer 322 is fed back via a resistor 359 to its input. Shared buffer 322 and resistor 359 establish an operational amplifier, as it is apparent for a person skilled in the art. The resistor 359 is an external, off-chip resistor, i.e. is neither integrated in the SLIC integrated circuit nor in the CODEC integrated circuit.

The shared buffer 322 provides for a highly linear and low noise output signal and may have switchable gain. For instance, for normal mode operation (voice transmission), the DC gain factor may be 30 and the AC gain factor may be 6. In case of ringing the buffer gain has to be enhanced e.g. up to a DC gain factor of 60. Then, a sinusoidal voltage of 2.4 V (peak value) at the input of the buffer 322 translates into nearly 150 V peak voltage across the subscriber line pair 302.

As depicted in FIG. 3, the battery voltage $V_{batt}$, i.e. the supply voltage for the SLIC 304, may be supplied by a DC-DC converter 360, 363. The DC-DC converter 360, 363 is used to provide an adequate DC voltage such that the SLIC 304 can generate the required DC voltage for maintaining the target current flow in the subscriber line pair 302. To this end, the DC-DC converter 360, 363 comprises a DC-DC external elements unit 360 and a DC-DC control logic circuitry 363 inside the CODEC circuit 305. The DC-DC external elements unit 360 may comprise, inter alia, a coil, a switching transistor and a diode. It is controlled by a control signal which is output by the DC-DC control logic circuitry 363 and received via control line 361. The DC-DC control logic circuitry 363 receives a feedback indicative of the generated voltage from the DC-DC external elements unit 360 via feedback line 364 and senses a voltage at a node between the output of the 9 bit DAC 316 and the input of the low pass filter 317 via control line 365.

The operation of DC-DC converter 360, 363 is as follows: If, in the normal operation mode, a certain DC voltage, say 24 V, has to be generated by the SLIC 304 across the subscriber line pair 302, a corresponding analog control voltage indicative of this desired subscriber line voltage shows up at the output of the 9 bit DAC 316. Based on this information, the DC-DC converter 360, 363 generates a sufficiently high battery voltage $V_{batt}$, for instance 32 V, which is sufficient to power the SLIC 304 under these circumstances. If, for another telephone connection, a higher DC voltage across the subscriber line pair 302, e.g. 40 V, is needed, the DC-DC external elements unit 360 is controlled via control line 361 to increase the output battery voltage $V_{batt}$ to satisfy the enhanced supply voltage demand of the SLIC 304. As an example, in this case the DC-DC external elements unit 360 may output a DC voltage $V_{batt}$=48 V.

In the ring mode, maximum $V_{batt}$ has to be substantially increased due to the high peak voltage needed across the subscriber lines 302. In this case, the output voltage $V_{batt}$ of the DC-DC external elements unit 360 traces the sinusoidal ring voltage, i.e. represents itself a sinusoidal voltage curve having a sufficiently high peak voltage. Same as in the shared buffer 322, the voltage transfer ratio in the DC-DC converter 360, 363 may be switched from a first gain factor for normal mode operation (e.g. gain factor 30) to a gain factor for ring mode operation (e.g. gain factor 60) in the DC-DC converter 360, 363.

Especially in the ring mode the sinusoidal output voltage $V_{batt}$ of the DC-DC external elements unit 360 should be essentially in phase tracking relationship to the sinusoidal SLIC output voltage across the subscriber line pair 302. Therefore, any possible phase shift between the control signal of the DC-DC external elements unit 360 received via control line 361 and the input signal of the SLIC 304 should be small. In this context, it is to be noted that the control signal for the DC-DC control logic circuitry 363 and thus for the DC-DC external elements unit 360 is tapped by control line 365 at the input of the low pass filter 317. As the low pass filter 317 has a cut-off frequency being substantially higher than the typical ring frequency (15 Hz to 60 Hz), the low pass filter 317 is operated during ringing completely in its pass-band regime where no or only a neglectable phase shift occurs between the filter input signal and the filter output signal. It is to be remembered that the high cut-off frequency of the low pass filter 317 was only made possible by the provision of the noise shaper 315 shifting the quantization noise to higher frequencies. Consequently, it is the provision of the noise shaper 315 which allows to tap the control signal of the DC-DC converter 360, 363 directly from the output of the 9 bit DAC 316, i.e. upstream of the low pass filter 317.

Tapping the control signal for the DC-DC converter 360, 363 at the input of the low pass filter 317 is beneficial in view of ESD (Electro Static Discharge) protection of the circuitry. As already mentioned, the capacitor 356 of the low pass filter 317 is an external (i.e. off-chip) capacitor and thus connected to a pin of the CODEC integrated circuit 305 which has to be protected against ESD. If the control signal of the DC-DC converter 360, 363 would be connected to the same pin (i.e. would be tapped from the output of the low pass filter 317), it would be necessary to guard transistors in the DC-DC converter 360, 363 against ESD. This would increase the silicon area needed for implementing the DC-DC converter 360, 363. In contrast thereto, according to the embodiment shown in FIG. 3, the low pass filter resistor 357 "isolates" the node where the control signal for the DC-DC converter 360, 363 is tapped from the pin for the external capacitor 356 and thus provides for an inherent or "built-in" ESD protection of the input of the DC-DC converter 360, 363, because its input is not directly connected to a pin. Therefore, the provision of the noise shaper 315 also allows to reduce the complexity of the analog part of the circuitry in view of ESD protection.

Basically, a DC-DC converter 360, 363 is not necessarily needed. Alternatively, the battery voltage $V_{batt}$ for the SLIC 304 could be generated by a constant DC voltage source (probably switchable between $V_{batt}$=48 V for normal mode operation and $V_{batt}$=150 V for ring mode operation). However, such arrangement would give rise to dissipation power losses in the normal operation mode and in the ring mode in cases where considerably less subscriber line voltage were needed at the output of the SLIC 304.

FIG. 5 illustrates an exemplary schematic of the noise shaper 315. The noise shaper 315 comprises a gain correction stage 501, a first adder 502, a MSBs (Most Significant Bits) output stage 503, a LSBs (Least Significant Bits) expand stage 504, a second adder 505 and a delay element 506. The input signal having a word width w1 (e.g. w1=16) is attenuated in the gain correction stage 501 to a maximum range of values which guarantees that the first adder 502 will not overflow. Thus, a no-saturation adder could be used for the first adder 502 which receives the input signal at a first input. The output of the first adder 502 is fed into the MSBs output stage 503 and into the positive input of the second adder 505. The MSBs output stage takes 9 MSBs from the 16 bit input and passes these 9 MSBs as a 9 bit word to the output of the noise shaper 315. According to the known function of a noise shaper, the 7 LSBs representing the quantization error are filtered in a feedback loop. Here, the 7 LSBs are calculated by the LSBs expand stage 504 expanding the output bit word to a 16 bit word by adding zeros as LSBs and by the second adder 505 subtracting this expanded output word from the 16 bit output word of the first adder 502. The 16 bit output word of the second adder 505 is the absolute value of the 7 LSBs of the 16 bit output word of the first adder 502. This quantization error is delayed in delay element 506 and fed back to a second input of the first adder 502.

If the noise shaper 315 is disabled via input 318, all components depicted in FIG. 5 are disabled and the actual output word provided by the MSBs output stage 503 is frozen. To this end, the noise shaper 315 may contain an additional buffer (not shown) for holding the latest 9 bit output word of the MSBs output stage 503 or the MSBs output stage 503 itself may be equipped with such bit word hold facility (which still needs to work during the switch-off phase of the noise shaper 315).

It is to be noted that the combination of a low resolution DAC 316 (with an output bit width of multiple bits, e.g. more than 5 bits) and a noise shaper 315 with enable/disable functionality is superior to the use of a sigma-delta DAC (which has a built-in filtering of the quantization error) because, inter alia, in a sigma-delta DAC the inherent noise shaping functionality can not be switched off.

The invention claimed is:

1. An apparatus that drives a subscriber line pair to a target DC line current, the apparatus comprising:
   a current detector that senses an actual DC line current on the subscriber line pair;
   a feedback loop that feeds back a control variable of the current based on the sensed actual DC line current;
   a noise shaper that shapes a control signal based on the control variable such that a quantizer error of the control signal is minimized;
   a generator that generates a DC line current to drive the subscriber line pair; and
   a controller that adjusts the control variable such that the actual DC line current is adjusted to be equal to the target DC line current.

2. The apparatus according to claim 1, wherein the noise shaper is configured to reduce the bit width of the sensed actual DC line current.

3. The apparatus according to claim 1, wherein the noise shaper is configured to be switched off during operation of the apparatus.

4. The apparatus according to claim 1, further comprising an oversampling circuit coupled to the output of the current detector.

5. The apparatus according to claim 4, wherein the oversampling circuit comprises: a first interpolation circuit configured to enhance a first sampling rate at an input of the oversampling circuit to an intermediate sampling rate.

6. The apparatus according to claim 5, wherein the oversampling circuit comprises: a second interpolation circuit configured to enhance the intermediate sampling rate to a second sampling rate at an output of the oversampling circuit.

7. The apparatus according to claim 6, wherein the second sampling rate is of the order of 1 MHz.

8. The apparatus according to claim 5, wherein the first sampling rate is of the order of 1 to 10 kHz.

9. The apparatus according to claim 5, wherein the intermediate sampling rate is of the order of 500 kHz.

10. The apparatus according to claim 4, wherein the oversampling circuit comprises a low pass filter for suppressing mirror frequencies.

11. The apparatus according to claim 1, further comprising a circuit that monitors a quantity indicative of a transient response of the digital control signal.

12. The apparatus according to claim 1, further comprising a disable circuit that disables the noise shaper if the quantity indicative of a transient response of the digital control signal is smaller than a threshold.

13. The apparatus according to claim 1, further comprising:
a digital-to-analog converter; and
a low pass filter that filters a signal converted by the digital-to-analog converter.

14. The apparatus according to claim 13, wherein a cut-off frequency of the low pass filter is higher than 100 Hz.

15. The apparatus according to claim 13, wherein a cut-off frequency of the low pass filter is higher than 500 Hz.

16. The apparatus according to claim 13, wherein a cut-off frequency of the low pass filter is about or higher than 1000 Hz.

17. The apparatus according to claim 13, wherein an output is electrically connected to a node located between the output of the digital-to-analog converter and the input of the low pass filter.

18. The apparatus according to claim 1, wherein the control signal is configured to drive an external power supply of a Subscriber Line Interface Circuit (SLIC).

19. The apparatus according to claim 1, wherein the actual DC line current represents voice data.

20. The apparatus according to claim 1, wherein the noise shaper is incorporated into a CODEC that receives voice data.

21. A method for driving a subscriber line pair to a target DC line current, the method comprising the steps of:
sensing an actual DC line current on the subscriber line pair;
feeding back a control variable of the current based on the sensed actual DC line current;
noise shaping a control signal based on the control variable such that a quantizer error of the control signal is minimized;
generating a DC line current to drive the subscriber line pair; and
controlling the control variable such that the actual DC line current is adjusted to be equal to the target DC line current.

22. The method according to claim 21 wherein the noise shaping step reduces the bit width of the sensed actual DC line current.

23. The method according to claim 21, wherein the noise shaping is switched off during normal operation.

24. The method according to claim 21, further comprising the step of oversampling the output of the current detector.

25. The method according to claim 24, wherein the oversampling comprises: a first interpolation configured to enhance a first sampling rate at an input of the oversampling circuit to an intermediate sampling rate.

26. The method according to claim 25, wherein the oversampling circuit comprises: a second interpolation circuit configured to enhance the intermediate sampling rate to a second sampling rate at an output of the oversampling circuit.

27. The method according to claim 26, wherein the oversampling circuit comprises a low pass filter for suppressing mirror frequencies.

28. The method according to claim 26, wherein the second sampling rate is of the order of 1 MHz.

29. The method according to claim 25, wherein the first sampling rate is of the order of 1 to 10 kHz.

30. The method according to claim 25, wherein the intermediate sampling rate is of the order of 500 kHz.

31. The method according to claim 21, further comprising the step of monitoring a quantity indicative of a transient response of the digital control signal.

32. The method according to claim 21, further comprising the step of disabling noise shaping if the quantity indicative of a transient response of the digital control signal is smaller than a threshold.

33. The method according to claim 21, further comprising the steps of:
digital-to-analog converting the control variable; and
low pass filtering a signal converted by the digital-to-analog converter.

34. The method according to claim 33, wherein a cut-off frequency of the low pass filtering is higher than 100 Hz.

35. The method according to claim 33, wherein a cut-off frequency of the low pass filtering is higher than 500 Hz.

36. The method according to claim 33, wherein a cut-off frequency of the low pass filtering is about or higher than 1000 Hz.

37. The method according to claim 21, wherein the control signal is configured to drive an external power supply of a Subscriber Line Interface Circuit (SLIC).

38. The method according to claim 21, wherein the actual DC line current represents voice data.

39. The method according to claim 21, wherein the noise shaping reduces the bit width of the sensed actual DC line current.

* * * * *